US007233641B2

(12) United States Patent
Hilderscheid et al.

(10) Patent No.: US 7,233,641 B2
(45) Date of Patent: Jun. 19, 2007

(54) METHOD AND CONTROL DEVICE FOR CONTROLLING THE TEMPERATURE OF A DETECTOR SYSTEM INSIDE A COMPUTED TOMOGRAPHY UNIT

(75) Inventors: Thomas Hilderscheid, Altdorf (DE); Helmut Winkelmann, Eggolsheim (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/985,010

(22) Filed: Nov. 10, 2004

(65) Prior Publication Data
US 2005/0100128 A1 May 12, 2005

(30) Foreign Application Priority Data
Nov. 10, 2003 (DE) ................. 103 52 382

(51) Int. Cl.
*G01N 23/00* (2006.01)
(52) U.S. Cl. .................... 378/19; 250/370.15
(58) Field of Classification Search .......... 378/19, 378/4; 250/370.15, 363.03
See application file for complete search history.

(56) References Cited

U.S. PATENT DOCUMENTS

| 4,969,167 | A | * | 11/1990 | Zupancic et al. ............. 378/19 |
| 4,991,193 | A | * | 2/1991 | Cecil et al. ................. 378/117 |
| 6,134,301 | A | * | 10/2000 | Mruzek et al. ............. 378/147 |
| 6,411,672 | B1 | * | 6/2002 | Sasaki et al. ................ 378/19 |
| 6,667,482 | B2 | | 12/2003 | Von Der Haar ........ 250/370.11 |
| 6,925,142 | B2 | | 8/2005 | Pohan et al. .................. 378/19 |

FOREIGN PATENT DOCUMENTS

| DE | 196 15 178 A1 | 10/1997 |
| DE | 197 40 212 A1 | 3/1999 |
| DE | 199 49 792 A1 | 4/2001 |
| DE | 199 49 793 A1 | 5/2001 |
| DE | 199 62 229 A1 | 7/2001 |
| DE | 101 16 222 A1 | 10/2002 |
| DE | 101 38 913 A1 | 8/2005 |

OTHER PUBLICATIONS

German Office Action dated Apr. 11, 2007.

* cited by examiner

*Primary Examiner*—Edward J. Glick
*Assistant Examiner*—Jurie Yun
(74) *Attorney, Agent, or Firm*—Harness, Dickey & Pierce, PLC

(57) ABSTRACT

A method and a control device are for controlling the temperature of a detector system inside a computed tomography unit. The CT unit includes a rotatable gantry with a gantry housing in which both an X-ray tube and the detector system are located. The detector system is arranged, in turn, inside a detector housing. The air temperature is set in the gantry housing via a temperature-controlled air circulation. The temperature of the ambient air of the detector housing is set by a control system that uses the temperature of the detector system as controlled variable.

18 Claims, 2 Drawing Sheets

METHOD AND CONTROL DEVICE FOR CONTROLLING THE TEMPERATURE OF A DETECTOR SYSTEM INSIDE A COMPUTED TOMOGRAPHY UNIT

The present application hereby claims priority under 35 U.S.C. §119 on German patent application number DE 103 52 382.0 filed Nov. 10, 2003, the entire contents of which are hereby incorporated herein by reference.

FIELD OF THE INVENTION

The invention generally relates to a method for controlling the temperature of a detector system inside a computed tomography unit. Preferably, the CT unit includes a rotatable gantry with a gantry housing in which both an X-ray tube and the detector system are located, the detector system being arranged, in turn, inside a detector housing, and the air temperature being set in the gantry housing by way of a temperature-controlled air circulation.

The invention also generally relates to a control device for controlling the temperature of a detector system inside a computed tomography unit. Preferably, the CT unit includes a rotatable gantry with a gantry housing in which both an X-ray tube and the detector system are located, the detector system being arranged, in turn, inside a detector housing, and the air temperature being set in the gantry housing by way of a temperature-controlled air circulation.

BACKGROUND OF THE INVENTION

It is generally known that the X-ray tube and also the electric components of a computed tomograph dissipate energy in the form of heat because of their strongly fluctuating power losses.

This heat can have a negative effect on the image quality of the CT unit, since relevant components are influenced by changes in temperature during generation of images. The detector modules and the associated evaluation electronics, for example, are such temperature-sensitive components.

Furthermore, there is a risk of overheating of individual components in the CT unit. The temperature inside the gantry of a CT unit is controlled for this reason.

The DMS (=Detector Measurement System) in the gantry of the CT unit is in particular need of very accurate temperature control. As a rule, DMS includes scintillators upstream of which collimators are positioned, and photodiodes that detect the incident radiation and then relay it in the form of analogue signals. The scintillators, the collimators and the photodiodes are temperature-sensitive components. Thus, for example, temperature fluctuations can lead to longitudinal expansions and/or longitudinal contractions that are seen in undesired deformations of these components. These deformations lead, inter alia, to shading that impairs the recorded CT image.

Two separate temperature control loops have been used to date in order to be able to ensure adequate temperature management.

Firstly, a control loop controls the air temperature inside the gantry interior. In this case, use is made for the most part of ventilation elements that are driven as a function of the temperature of the gantry interior. At least one sensor determines the temperature in the interior of the gantry in this case.

An additional control loop is used for the DMS, because the temperature-sensitive DMS can be exposed to very different ambient air temperatures. Owing to the rotating gantry, the DMS can, for example, be positioned on one occasion in a thermally favorable way in front of a fan outlet, and be positioned in a thermally unfavorable fashion on another occasion.

The second control loop of the DMS mostly includes one or more controlled fans at DMS or, in the "warm-up phase of the CT unit", heating elements inside the DMS. The temperature in the DMS that was measured using a sensor in the latter was used as controlled variable of the fans/heating elements.

This way of separately controlling the temperature of the DMS and interior of the gantry is particularly complicated.

SUMMARY OF THE INVENTION

It is an object of an embodiment of the invention to find a possible way of controlling the temperature of a DMS that is easier to implement by comparison with the known methods and devices.

The inventors have found that optimum temperature control of the DMS—that is to say, the observance of specific limits for the temperature—is decisive for generating CT images of high quality. The temperature limits or the temperature control in the interior of the gantry is not as decisive for optimum image generation as the DMS temperature control. If the temperature control of the interior of the gantry is controlled by way of a temperature sensor that is located inside the DMS housing, the DMS can be subjected to temperature control more effectively and more simply within the desired temperature limits. This comes about because the temperature in the interior of the gantry corresponds to the desired temperature of the DMS, and additionally because the thermal capacity of the gantry's fluctuations of the DMS, which has a lower thermal capacity than the gantry, can be compensated more effectively in thermal terms.

In accordance with the general idea of an embodiment of the invention, the inventors propose to improve the known method for controlling the temperature of a detector system inside a computed tomography unit, the CT unit having a rotatable gantry with a gantry housing in which both an X-ray tube and the detector system are located, the detector system being arranged, in turn, inside a detector housing, and the air temperature in the gantry housing being set by means of a temperature-controlled air circulation, to the effect that the temperature of the ambient air of the detector housing is set by a control system that uses the temperature of the detector system as controlled variable.

It is thereby achieved that the temperature of the DMS can be set to a desired temperature value, and that no further components such as fans or heating mats and their controllers, in particular in the DMS, need be used. It is thereby possible to save hardware components and thus costs. However, the gain in space owing to the saving of these components inside the interior of the gantry is seen as particularly advantageous.

It is true that saving fans, for example, results in larger temperature fluctuations in the interior of the gantry that can be more effectively detected by the use of further temperature sensors at the components to be protected. However, these larger temperature fluctuations in the interior of the gantry have a less disturbing effect, since the components in the interior of the gantry have a larger permissible temperature range.

A further advantage resulting from the novel method is that the temperature control can be more easily implemented, since the influence of disturbance variables on the controlled system is lessened.

It is also advantageous for the method when the control system sets the temperature-controlled air circulation in the gantry housing. It is possible thereby to adapt the temperature in the interior of the gantry in a particularly simple way to the desired temperature of the DMS.

The temperature of the detector system can be measured directly at a wall of the detector housing, it being best for the temperature sensor to be connected to the wall in a thermally conducting fashion. Attaching the temperature sensor in this way to the wall can facilitate rapid detection of the ambient temperature of the DMS, as a result of which the ambient temperature can then be varied with corresponding rapidity.

It is favorable when the temperature of the detector system is measured directly at the inside of the detector housing. The temperature sensor can thereby be attached in a fashion protected by the DMS housing, and will be protected against interference, for example being inadvertently touched during maintenance work inside the interior of the gantry.

A further possibility resides in measuring the temperature directly at the collimator of the detector system. The collimator, which is an essential constituent of the DMS, is exposed to the temperature fluctuations of the DMS and can therefore also exhibit larger twists because of the longitudinal expansion. These twists have a disturbing effect on the image acquisition in the DMS by shading scintillators. If the temperature sensor is attached to the collimator, temperature variations that have a disturbing effect on the image acquisition can be detected and thus corrected yet more rapidly.

As an alternative, however, it is also possible to measure the temperature of the detector system in the detector housing. The next temperature of scintillator, collimator and photodiodes can thereby be measured particularly easily.

It is advantageous for the method to measure the temperature of the detector system and at least one site. If, however, the temperature is determined at a number of sites in the DMS, a spatial temperature profile or a temperature created between the DMS and the ambient temperature can be ascertained very easily. Knowledge of the magnitude of the temperature gradient can be used to adapt the ambient air more rapidly and effectively.

A good thermal conductivity as a connection between the detector housing and gantry housing is advantageous for the method.

It is advantageous, furthermore, that the temperature of further temperature-sensitive modules, preferably of the X-ray tube of the detector system, is measured at at least one site and in the event of overshooting of a maximum permissible temperature on the cooling power is raised independently of the temperature sensor, or the CT unit including the X-ray tube is switched off. The safety risk in the case of undesired escape of radiation can thereby be reduced.

In accordance with an embodiment of the novel method, the inventors also propose control device for controlling the temperature of a detector system inside a computed tomography unit, the CT unit having a rotatable gantry with a gantry housing in which both an X-ray tube and a detector system are located, the detector system being arranged, in turn, inside a detector housing, and the air temperature being set in the gantry housing by way of a temperature-controlled air circulation, the control device being characterized in that it has a connection for temperature-controlled air circulation, and in that the temperature of the detector system is used as controlled variable in order thus to undertake a setting of the temperature of the ambient air of the detector housing.

The control device also permits the temperature of the DMS to be set easily to a desired temperature value without the need for further components such as fans or heating mats and their controllers, in particular in the DMS, needing to be used. The control device can be attached, for example, outside the interior of the gantry, the result being to enable a gain in space in the interior of the gantry by saving controllers.

BRIEF DESCRIPTION OF THE DRAWINGS

The invention is described below with reference to preferred exemplary embodiments with the aid of FIGS. 1 to 4, the following abbreviations being used in the figures: 1: gantry; 2: X-ray tube; 3: DMS; 3.1: DMS housing; 3.2: scintillator; 3.3: collimator; 3.4: photodiode; 3.5: temperature sensor in the DMS; 4: temperature sensor in the interior of the gantry; 5: cold feed into the interior of the gantry; 6: heat removal from the interior of the gantry; 7: cold feed into the DMS; 8: heat removal from the DMS; 9: control unit of the CT unit; 10: temperature control loop of the DMS; 11: temperature control loop of the gantry; 12: control device; 13: temperature sensor at the X-ray tube.

In detail, of the figures.

DETAILED DESCRIPTION OF THE EXEMPLARY EMBODIMENTS

Figure 1:
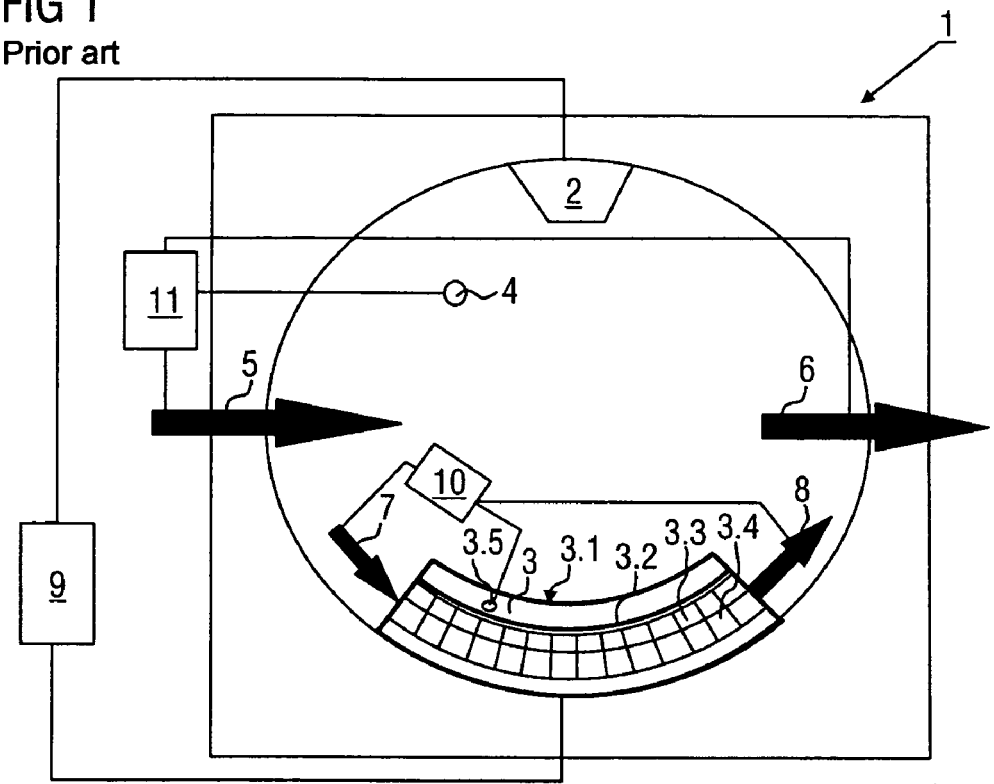
FIG. 1 shows a diagram that explains the previously known cooling process in the gantry.

FIG. 1 shows a diagram that is intended to explain the previously known cooling process in the gantry 1. A control unit 9 of the CT unit coordinates the rotary and the translatory movement in the gantry 1. The control unit 9 of the CT unit also controls the X-ray tube 2 and the DMS 3 during imaging.

Located in the gantry 1 is an essential component of the CT unit—the X-ray tube 2, which outputs its power loss into the interior of the gantry chiefly as heat. In order to be able to dissipate this heat, which has an interfering effect for specific components, use is made of a cooling process that determines and controls the temperature in the interior of the gantry. A temperature sensor 4 determines the temperature in the interior of the gantry and relays the measured data to the temperature control loop 11 of the gantry 1. If required, the temperature control loop 11 of the gantry 1 controls the cold feed 5 into the interior of the gantry and/or the removal 6 of heat from the interior of the gantry.

A DMS 3 is also located in the gantry 1. This DMS 3, which is mostly embedded in a housing 3.1, chiefly comprises the scintillators 3.2, the collimators 3.3 and the photodiodes 3.4. These components are very temperature-sensitive, and require a relatively limited temperature range by comparison with the interior of the gantry.

By way of example, the DMS should be controlled in a temperature window of approximately +/−2 kelvins about an optimum operating temperature, while a temperature to be set in the range of approximately +10 degrees Celsius to approximately +40 degrees Celsius is sufficient for the interior of the gantry.

For this reason, a dedicated additional cooling process is used for the DMS 3. For this purpose, the temperature in the interior of the DMS housing 3.1 is determined via a temperature sensor 3.5 located in the DMS 3. This temperature sensor 3.5 relays the measured data to a temperature control loop 10 of the DMS, which then controls both the cold feed 7 into the DMS 3 and the removal 8 of heat from the DMS 3. The cold feed 7 and the removal 8 of heat can be implemented by a fan, for example.

Note: the figures do not illustrate heating elements nor the heat feed into the gantry 1 and in the DMS 3, which are generally used during the warm-up phase of the CT unit in order to ensure that the optimum operating temperature of the gantry and of the DMS 3 is reached.

A disadvantage of this cooling process is that the temperature control must fulfill different cooling requirements depending on the position of the DMS 3, which can rotate in the gantry 1 during a CT recording. The cooling process to date is, however, too slow for this purpose. A further disadvantage of this known method is that the two separate cooling processes for the DMS 3 and the gantry 1 are relatively complicated and therefore raise the costs of a CT unit owing to the separate cooling components.

Figure 2:
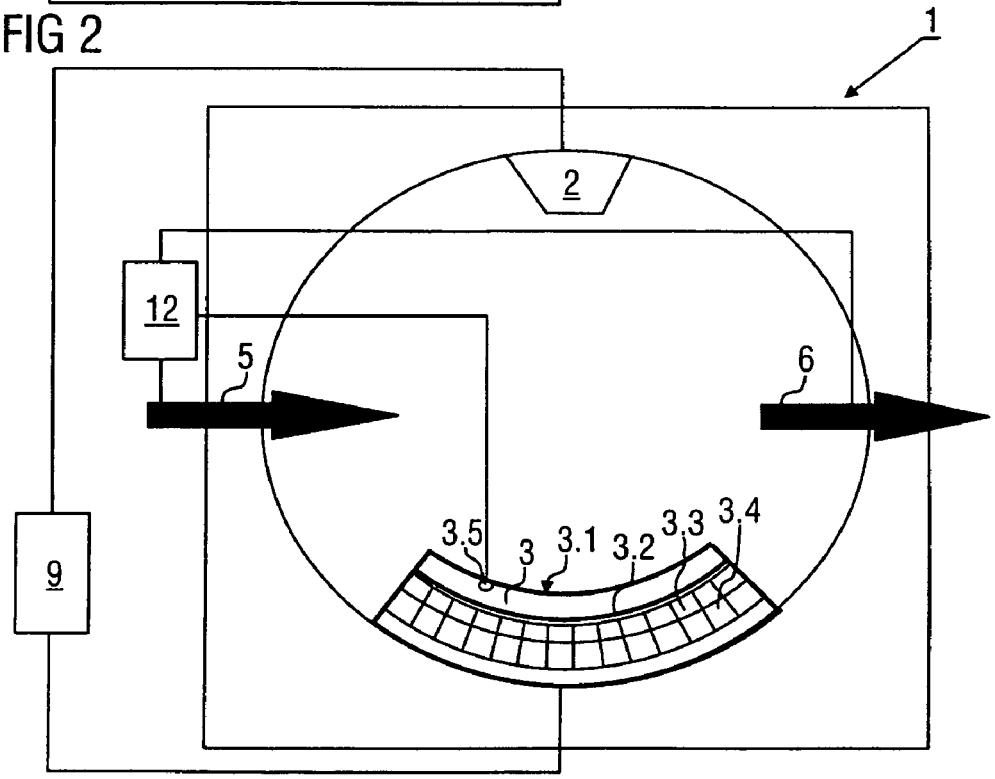
FIG. 2 shows a diagram that explains the novel cooling process in the gantry.

FIG. 2 shows a diagram that is intended to explain the novel cooling process in the gantry 1. In a way shown in FIG. 1, a control unit 9 of the CT unit coordinates the rotatory and the translatory movements of the gantry 1, and also controls the X-ray tube 2 and the DMS 3 during CT imaging. By contrast with the cooling process from FIG. 1, a novel control device 12 that uses a temperature sensor 3.5 to pick up the temperature in the DMS 3 as measured variable controls the cold feed 5 into the interior of the gantry and/or the removal 6 of heat from the interior of the gantry.

The control device 12 differs from the temperature control loop 11 of the gantry 1 from FIG. 1 in that the temperature limiting values, that is to say the upper and lower limits of the temperature of the DMS 3, are set. The cold feed 5 and/or the removal 6 of heat are adapted to the temperature requirements of the DMS 3. Since the ambient temperature is set to the desired value by means of the cold feed 5/removal 6 of heat into/from the interior of the gantry of the DMS 3, an additional control device for the DMS 3, for example having a controlled fan, is no longer required.

Figure 3:
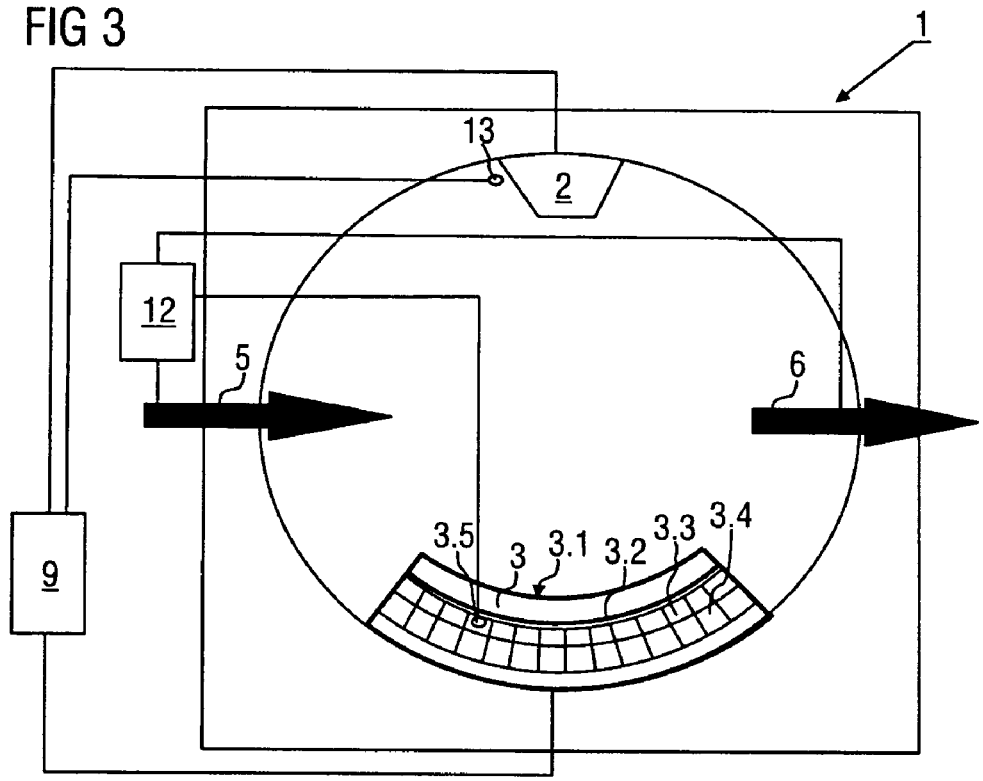
FIG. 3 shows a diagram of FIG. 2, but with a changed arrangement of the temperature sensor in the DMS and an additional temperature sensor.

In a similar way to FIG. 2, FIG. 3 shows a diagram that explains the novel method for controlling the temperature of a detector system inside a computed tomography unit. In addition to the temperature sensor 3.5 in the DMS 3, which determines the controlled variable for the control device 12, a temperature sensor 13 is fitted in the vicinity of the X-ray tube 2. If the temperature in the vicinity of the X-ray tube 2 is measured by the temperature sensor 13, the cooling power can be raised independently of the temperature sensor 3.5 upon overshooting of a maximum permissible temperature, or the CT unit including the X-ray tube 2 can be switched off.

Figure 4:
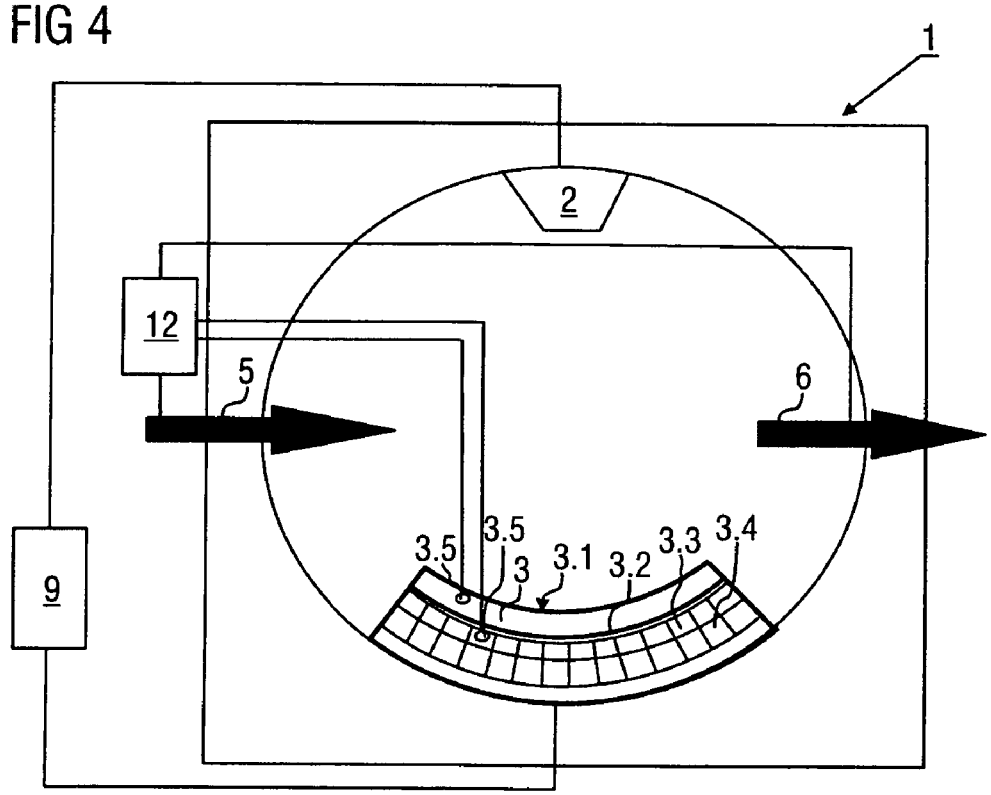
FIG. 4 shows a diagram that explains the novel cooling process in the gantry, with a number of temperature sensors in the gantry.

FIG. 4 shows a further embodiment. Two temperature sensors 3.5 are located in the DMS 3. One temperature sensor is fitted on the inside of the DMS housing 3.1. The other temperature sensor 3.5 is fitted in the collimator 3.3. It is possible thereby, for example, to detect a temperature gradient inside the DMS 3 particularly effectively. The cold feed 5 and/or the removal 6 of heat can then be controlled by the control device 12 as a function of the magnitude of the temperature gradient.

Overall, an embodiment of the invention provides a method and a novel control device for controlling the temperature of a detector system inside a computed tomography unit that is easier to implement by comparison with the known methods and devices.

The descriptions relating to FIGS. 1 to 4 are concerned chiefly with the cooling of the interior of the gantry, since a CT unit generally radiates heat during operation. The novel method for controlling the temperature of a detector system, and the control device are, however, also suitable for setting the DMS and the interior of the gantry to a desired operating temperature by means of heating elements.

It goes without saying that the features of the invention that are named above can be used not only in the combination respectively specified, but also in other combinations or on their own, without departing from the scope of the invention.

The following abbreviations have been used in the text of the application, the description of the figures and the patent claims:
CT computed tomograph
DMS Detector Measurement System

What is claimed is:

1. A method for controlling the temperature of a detector system inside a computed tomography unit, the CT unit including a rotatable gantry with a gantry housing in which both an X-ray tube and the detector system are located, the detector system being arranged inside a detector housing and the air temperature being set in the gantry housing via a temperature-controlled air circulation, the method comprising:
    setting the temperature of the ambient air external of the detector housing using a control system that uses the temperature of the detector system as a controlled variable.

2. The method as claimed in claim 1, wherein the control system sets the temperature-controlled air circulation in the gantry housing.

3. The method as claimed in claim 2, wherein the temperature of the detector system is measured directly at a wall of the detector housing, the temperature sensor being connected to the wall in a thermally conducting fashion.

4. The method as claimed in claim 3, wherein the temperature of the detector system is measured directly at the inside of the detector housing.

5. The method as claimed in claim 1, wherein the temperature of the detector system is measured directly at a wall of the detector housing, a temperature sensor being connected to the wall in a thermally conducting fashion.

6. The method as claimed in claim 5, wherein the temperature of the detector system is measured directly at the inside of the detector housing.

7. The method as claimed in claim 1, wherein the detector system includes a collimator, and wherein the temperature is measured directly at the collimator.

8. The method as claimed in claim 1, wherein the temperature of the detector system is measured in the detector housing.

9. The method as claimed in claim 1, wherein the temperature of the detector system is measured at at least one site.

10. The method as claimed in claim 1, wherein the thermal conductivity at the connection between the detector housing and gantry housing is improved.

11. The method as claimed in claim 1, wherein the temperature of further temperature-sensitive modules is measured at at least one site and, in the event of overshooting of a maximum permissible temperature, at least one of the cooling power is raised independently of the temperature sensor and the CT unit including the X-ray tube is switched off.

12. The method as claimed in claim 1, wherein the temperature of the X-ray tube of the detector system is measured at at least one site and, in the event of overshooting of a maximum permissible temperature, at least one of the cooling power is raised independently of the temperature sensor and the CT unit including the X-ray tube is switched off.

13. A control device for controlling the temperature of a detector system inside a computed tomography unit, the CT unit having a rotatable gantry with a gantry housing in which both an X-ray tube and the detector system are located, the detector system being arranged inside a detector housing, and the air temperature being set in the gantry housing via a temperature-controlled air circulation, the control device comprising:

a circuit for controlling the temperature of inflowing and outflowing air in the gantry housing, the circuit being connected to the detector system by a temperature sensor, and the circuit using sensor data from the temperature sensor as a control variable to set the temperature of the ambient air of the detector housing.

14. A method for controlling the temperature of a detector system inside a computed tomography unit, the detector system being arranged inside a detector housing and the air temperature being set in the housing via a temperature-controlled air circulation, the method comprising:

using the temperature of the detector system as a controlled variable to set the temperature of the ambient air external of the detector housing.

15. The method as claimed in claim 14, wherein the temperature of the detector system is measured directly at a wall of the detector housing, with a temperature sensor being connected to the wall in a thermally conducting fashion.

16. The method as claimed in claim 15, wherein the temperature of the detector system is measured directly at the inside of the detector housing.

17. The method as claimed in claim 14, wherein the detector system includes a collimator, and wherein the temperature is measured directly at the collimator.

18. The method as claimed in claim 14, wherein the temperature of the detector system is measured in the detector housing.

* * * * *